United States Patent
Wong et al.

(10) Patent No.: US 10,510,436 B2
(45) Date of Patent: Dec. 17, 2019

(54) USING SERIAL DILUTIONS OF REFERENCE SAMPLES TO CONSTRUCT A REFERENCE TABLE FOR SIGMOIDAL FITTING IN REAL-TIME PCR COPY NUMBER ANALYSIS

(71) Applicant: Credo Biomedical Pte Ltd., Singapore (SG)

(72) Inventors: Jr. Winston Wong, New Taipei (TW); Stephen Chang-Chi Kao, New Taipei (TW); Ying-Ta Lai, New Taipei (TW); Yih-Jyh Shann, New Taipei (TW); Ming-Fa Chen, New Taipei (TW); Chih-Rong Chen, New Taipei (TW)

(73) Assignee: Credo Biomedical Pte Ltd., Singapore (SG)

( * ) Notice: Subject to any disclaimer, the term of this patent is extended or adjusted under 35 U.S.C. 154(b) by 651 days.

(21) Appl. No.: 15/201,623

(22) Filed: Jul. 5, 2016

(65) Prior Publication Data
US 2018/0011967 A1  Jan. 11, 2018

(51) Int. Cl.
*G16B 30/00* (2019.01)
*C12Q 1/686* (2018.01)

(52) U.S. Cl.
CPC ............. *G16B 30/00* (2019.02); *C12Q 1/686* (2013.01)

(58) Field of Classification Search
None
See application file for complete search history.

(56) References Cited

U.S. PATENT DOCUMENTS

2014/0005066 A1  1/2014  Boles
2014/0272991 A1  9/2014  Vijaysri Nair

FOREIGN PATENT DOCUMENTS

| CN | 101532063 A | 9/2009 |
|---|---|---|
| EP | 1 632 580 A2 | 3/2006 |
| JP | 2014-23435 A | 2/2014 |
| JP | 2016-513473 A | 5/2016 |
| WO | 2016/006612 A1 | 1/2016 |

OTHER PUBLICATIONS

Tichopad, Ales, et al. "Standardized determination of real-time PCR efficiency from a single reaction set-up." Nucleic acids research 31.20 (2003): e122-e122.*
Ronaghi, Mostafa, Mathias Uhlén, and Pål Nyrén. "A sequencing method based on real-time pyrophosphate." Science 281.5375 (1998): 363-365.*
Tichopad, Ales, Anamarija Dzidic, and Michael W. Pfaffl. "Improving quantitative real-time RT-PCR reproducibility by boosting primer-linked amplification efficiency." Biotechnology Letters 24.24 (2002): 2053-2056.*
Liu et al., Validation of a quantitative method for real time PCR kinetics, Biochem Biophys Res Commun. Jun. 7, 2002;294(2):347-53.
Bernardo Acácio Santini Pereira et al., Expression of infection-related genes in parasites and host during murine experimental infection with Leishmania (Leishmania) amazonensis, Contents lists available at SciVerse ScienceDirect Microbial Pathogenesis, Aug. 18, 2011, pp. 101-108, XP028356063.
Robert G Rutledge et al., A kinetic-based sigmoidal model for the polymerase chain reaction and its application to high-capacity absolute quantitative real-time PCR, BMC Biotechnology, May 8, 2008, pp. 1-28, Biomed Central Ltd., XP021035719.
Rasmus Goll et al., Evaluation of absolute quantitation by nonlinear regression in probe-based real-time PCR, BMC Bioinformatics, Mar. 3, 2006, pp. 1-11, BioMed Central Ltd., XP021013610.

* cited by examiner

*Primary Examiner* — G Steven Vanni
(74) *Attorney, Agent, or Firm* — Winston Hsu

(57) ABSTRACT

The present invention discloses a method of real-time quantification of a target nucleic acid in a sample by constructing a reference table of copy number vs. designated parameter from reference samples which sharing the same nucleic acid sequences with the target nucleic acid. The method includes (a) constructing a reference table of copy number vs. designated parameter from reference samples; (b) amplifying the target nucleic acid; (c) monitoring and detecting the amplification of the target nucleic acid in real-time; (d) analyzing the detected signals to get the designated parameter of the target nucleic acid; and (e) looking up and interpolating to the reference table to get the copy number of the target nucleic acid.

6 Claims, 15 Drawing Sheets
Specification includes a Sequence Listing.

USING SERIAL DILUTIONS OF REFERENCE SAMPLES TO CONSTRUCT A REFERENCE TABLE FOR SIGMOIDAL FITTING IN REAL-TIME PCR COPY NUMBER ANALYSIS

BACKGROUND OF THE INVENTION

1. Field of the Invention

This present disclosure related to the field of nucleic acid quantification with the aid of quantitative real time PCR.

2. Description of the Prior Art

Nowadays, the methods for the quantification of nucleic acids are important in many fields of molecular biology, especially in the field of molecular diagnostics. Quantitative PCR (hereinafter qPCR) is considered as one of the most sensitive methods for quantifying gene expression level and is becoming a common tool for detecting and quantifying expression profiles of selected genes.

To date, absolute quantification is the most common approach used to perform quantitative amplification. That is, for each qPCR, it is required to amplify several serial-diluted standard controls with known concentrations of identical nucleic acid sequence in the same amplification reaction. Standard curves are produced by detecting the fluorescent signals, which are served as references. The concentration of the unknown samples is then obtained by interpolation with using the standard curves.

However, there are several drawbacks and limitations for the said method. First, the amount of reagents to use is huge for constructing standard curves, since it is necessary to obtain standard curves for each qPCR regardless of the amount of the unknown samples. This is crucial since the Cycle Threshold values, or called "Ct values", of the standard curves is required to enable interpolation so as to obtain the copy number of the unknown samples. The huge consumption of the reagents and controls leads to increased cost to carry out each qPCR, resulting in increasing testing fees.

Second, absolute quantification uses Ct values of each standard control as indexes for interpolating calculations to obtain the copy number of the unknown sample. Yet, the definition of Ct values is subject to manufacturers, whom also conduct varying calibration methods. In addition, there are lots of external factors that would affect the determination of the Ct values. Results suggest that even when the qPCRs are carried out on the same nucleic acid sequence by using the same instrument with identical amplification conditions at a fixed concentration, there are still variations between Ct values, since it may be obtained by different operators or distinct amplification repeats. Hence, in order to calculate the correct copy number of any unknown samples, it is required for the serial-diluted standard controls to be amplified along with the unknown samples to keep the external variables constant.

Third, even in the same qPCR test, where background values and all manipulation variations are neglected, the concentration of the reagents would still affect Ct values. Such variations cannot be overlooked. For example, if an amplification is performed with only the primer concentration variable, calibration of the constant standard curve of each samples with different primer concentration is still required to obtain the DNA copy number.

In summary, the Ct value itself is not an absolute, and could only represent the cycle number of a certain PCR sample amplification when it reaches a specific status. The value would therefore vary by experiments due to different conditions, and the absolute value of the Ct value itself could not be of any reference. That is, in spite of the high accuracy in obtaining the copy number using the current method, the complicated operational procedure required professionally trained operator to conduct as to minimize the manipulation variations.

Current real-time qPCR utilizes Ct values to perform either absolute or relative quantitation of a target sample. Both methods, however, are subject to a few assumptions: (1) The amplification at exponential phase is not limited by the exhaustion of the reagents (i.e., amplification efficiency is $\approx 1$); (2) The amplification efficiency is constant; and (3) The amplification efficiency of the standards and the target samples are identical.

W. Liu and D. A. Saint 2002 proposed a new mathematical model for line-fitting by using the sigmoidal curve fitting in *Biochemical and Biophysical Research Communications* p. 347-353, vol. 294 2002, which defined cycle number based on 2 factors: the fluorescence signals for each cycle, and the slope factor of the increased fluorescence dye strength during amplification. However, the proposed method is not practical.

To improve the above-mentioned problems, we hereby proposed a new method for absolute qPCR. Firstly, we standardize the copy number to its designated parameters by amplifying its serial diluted reference samples, and create a reference table through calibration. Secondly, we calibrated the results of the target nucleic acid by using the same analyzing method, and that the copy number is then obtained by referencing its designated parameters to the reference table. Through the present invention, the operator does not need to perform quantification of multiple standards along with the unknown samples, and the copy number is independent of Ct value.

SUMMARY OF THE INVENTION

Briefly, aspects of the present disclosure are directed to a method of real-time quantification of nucleic acid, which overcome the disadvantages of the prior art as mentioned above. The object of the present disclosure is in particular to provide methods for the quantification of the target nucleic acid (hereinafter, target sample) which the target sample is quantified independently without the need to perform the standard curve from time to time. This invention will not only provide a new quantifying method, but will also propose a new standard operational method that eliminates the Ct variation of qPCR which is relating to accompanying amplification efficiency, polymerase activity, primer concentration, and instrument variations.

In the present disclosure, the amplification of both reference samples and target sample(s) may be monitored by optical signals (fluorescent signals, phosphorescent signal, and etc.) and the chemical sensors (hydrogen ion, pyrophosphate and etc.) as long as they are proportional to the amplifications.

According to one aspect of the present disclosure, the method in a preferred embodiment includes: a) constructing a reference table of copy number vs. designated parameter; b) amplifying the target sample(s); c) measuring the amplification of the target sample(s) in real-time; d) analyzing the detected signals to get the designated parameter of the target sample (s); and e) looking up and interpolating to the reference table to get the copy number of the target sample(s). Among them, the reference table is calibrated and monitored by: i.) preparing and amplifying the reference samples; ii.) measuring the amplifications of the reference samples in real-time; iii.) analyzing the detected signals to get the designated parameter of each reference samples; and iv.) constructing the reference table of copy v.s designated parameters. The detected signals of target sample (s) would be analyzed with the same process as reference samples.

According to another aspect of the present disclosure, the detected signals of both reference samples and the target sample(s) would be analyzed by two-parametric sigmoid function and normalizing process.

This SUMMARY is provided to briefly identify some aspects of the present disclosure that are further described below in the DESCRIPTION. This SUMMARY is not intended to identify key or essential features of the present disclosure nor is it intended to limit the scope of any claims.

The term "aspects" is to be read as "at least one aspect." The aspects described above and other aspects of the present disclosure described herein are illustrated by way of example (s) and not limited in the accompanying drawing.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

A more complete understanding of the present disclosure may be realized by reference to the accompanying drawing in which.

DETAILED DESCRIPTION

The following merely illustrates the principles of the present disclosure. It will thus be appreciated that those skilled in the art will be able to devise various arrangements which, although not explicitly described or shown herein, embody the principles of the disclosure and are included within its spirit and scope.

Furthermore, all examples and conditional languages recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents including both currently known equivalents as well as equivalents developed in the future, i.e., any elements later developed that perform the same function, regardless of structure.

Unless otherwise explicitly specified herein, the drawings are not drawn to scale.

Figure 1:
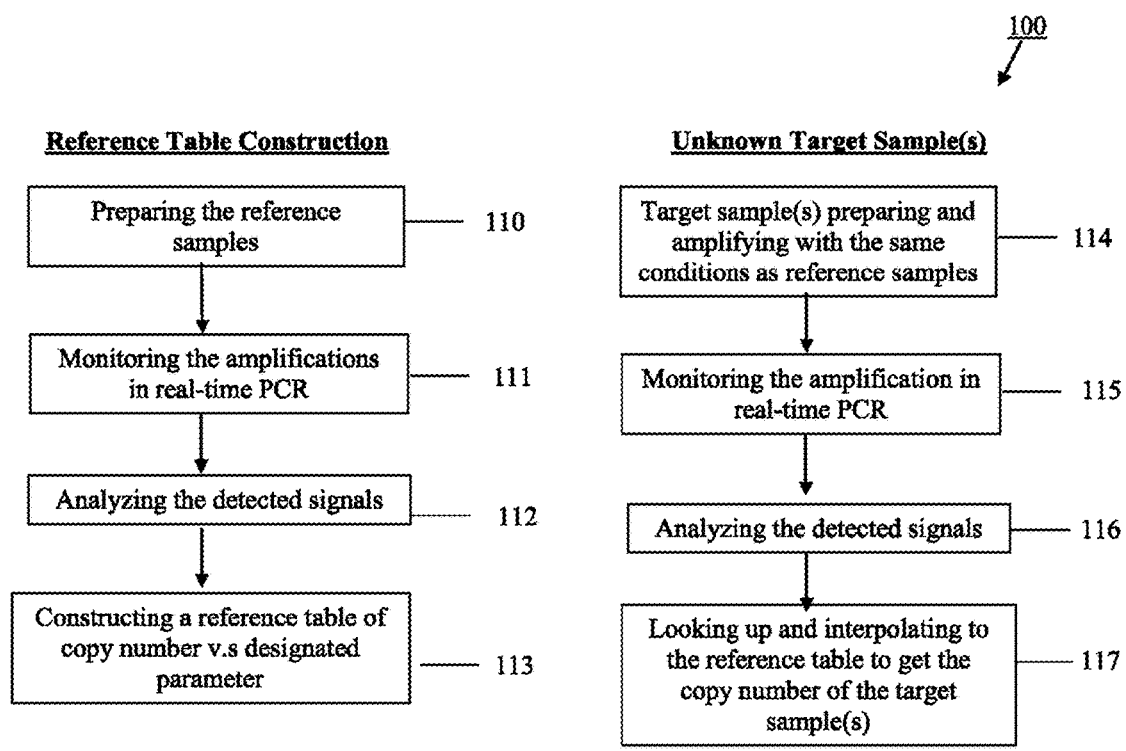
FIG. 1 illustrates one embodiment of a process for constructing a reference table of copy number vs. designated parameter.

As shown in FIG. 1, the present invention directs to a real-time quantification method of nucleic acid. FIG. 1 illustrate one embodiment of a method 100 that may be used to construct a reference table from the reference samples to provide information of the copy number vs. designated parameter which is useful in performing quantitation calculations. In one aspect, the method of constructing a reference table may be adapted to operating in real-time PCR processes wherein quantification calculations are performed by looking up and interpolating to the reference table to get the copy number of the target sample(s) where the target sample(s) is/are sharing the same nucleic acid sequences with the reference samples and amplifying with the same conditions.

The method 100 commences by preparing the reference samples 110 and measuring the amplification in real-time 111. The amplification of both reference samples and the target sample (s) may be monitored in real-time by monitoring the optical signals (fluorescent signals, phosphorescent signal, and etc.) which are generated during the amplification, or the chemical sensors (hydrogen ion, pyrophosphate, and etc.) which are the by-products of the amplification or other specific materials, as long as they are proportional to the amplifications.

Once the amplification completes, the detected signals are analyzed from the reference samples 112, and the reference table is then constructed using the copy number vs. designated parameter information 113. The target sample(s) is/are then amplified under the same condition 114, while measuring its amplification in real-time 115. After analyzing the detected signals 116, the copy number of the target sample(s) is/are known by comparing the value of the designated parameters to the reference table 117. Using this new quantifying approach proposed by this disclosed invention, the variations accompanying amplification efficiency, polymerase activity, primer concentration, and the instrument variations can be eliminated.

In another embodiment of the present invention, the amplification of the reference samples and the target sample(s) are monitored by adding EvaGreen® dye which can emit the fluorescent signal during amplification. The EvaGreen® dye could be replaced by other materials (SYBR®1 Dye, molecular beacon, probe, and etc.) which generated the optical signals (fluorescent signals, phosphorescent signal, and etc.) during the amplification, or the chemical sensors (hydrogen ion, pyrophosphate and etc.) which are by-products of the amplification or other specific materials, as long as they are proportional to the amplifications.

Figure 2:
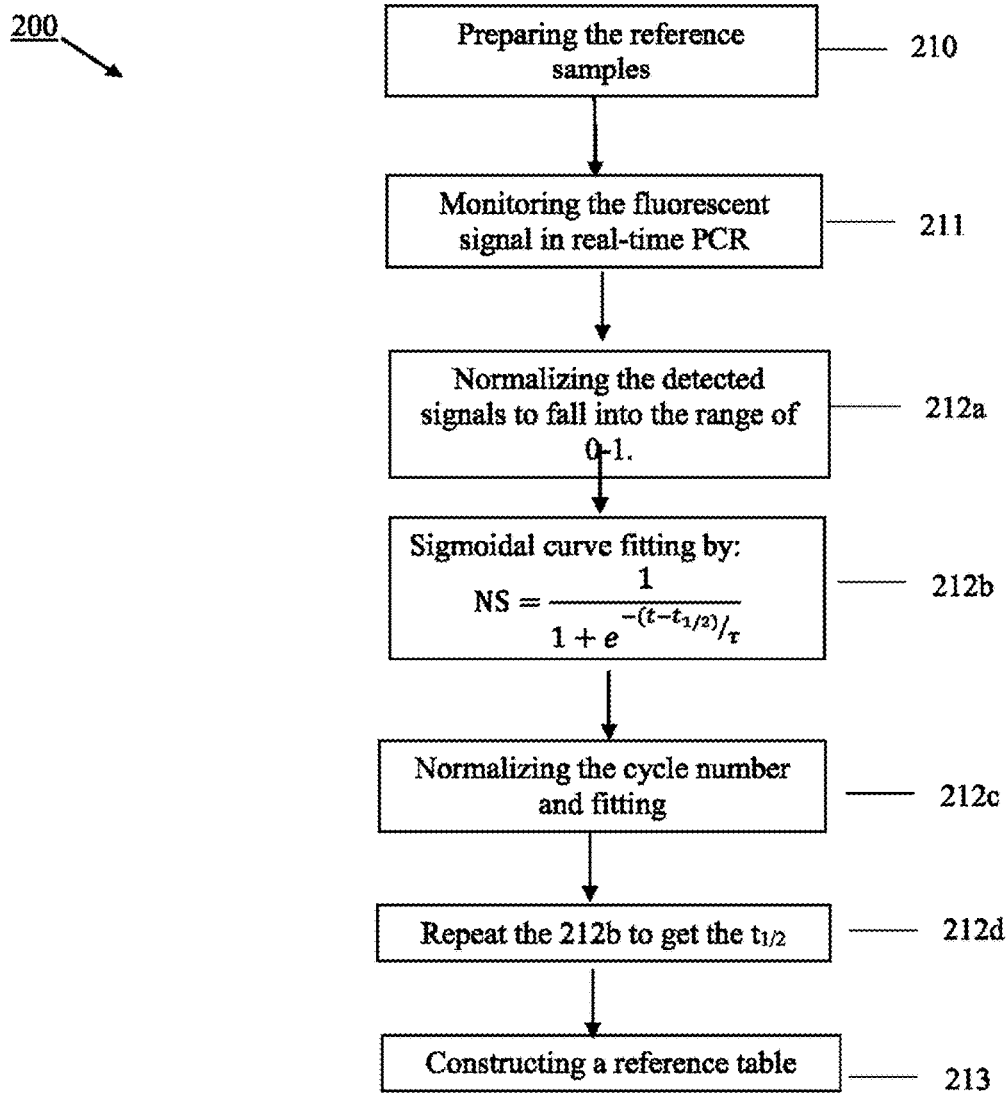
FIG. 2 illustrates another embodiment of a process for constructing a reference table of copy number vs. designated parameter.
Figure 3:
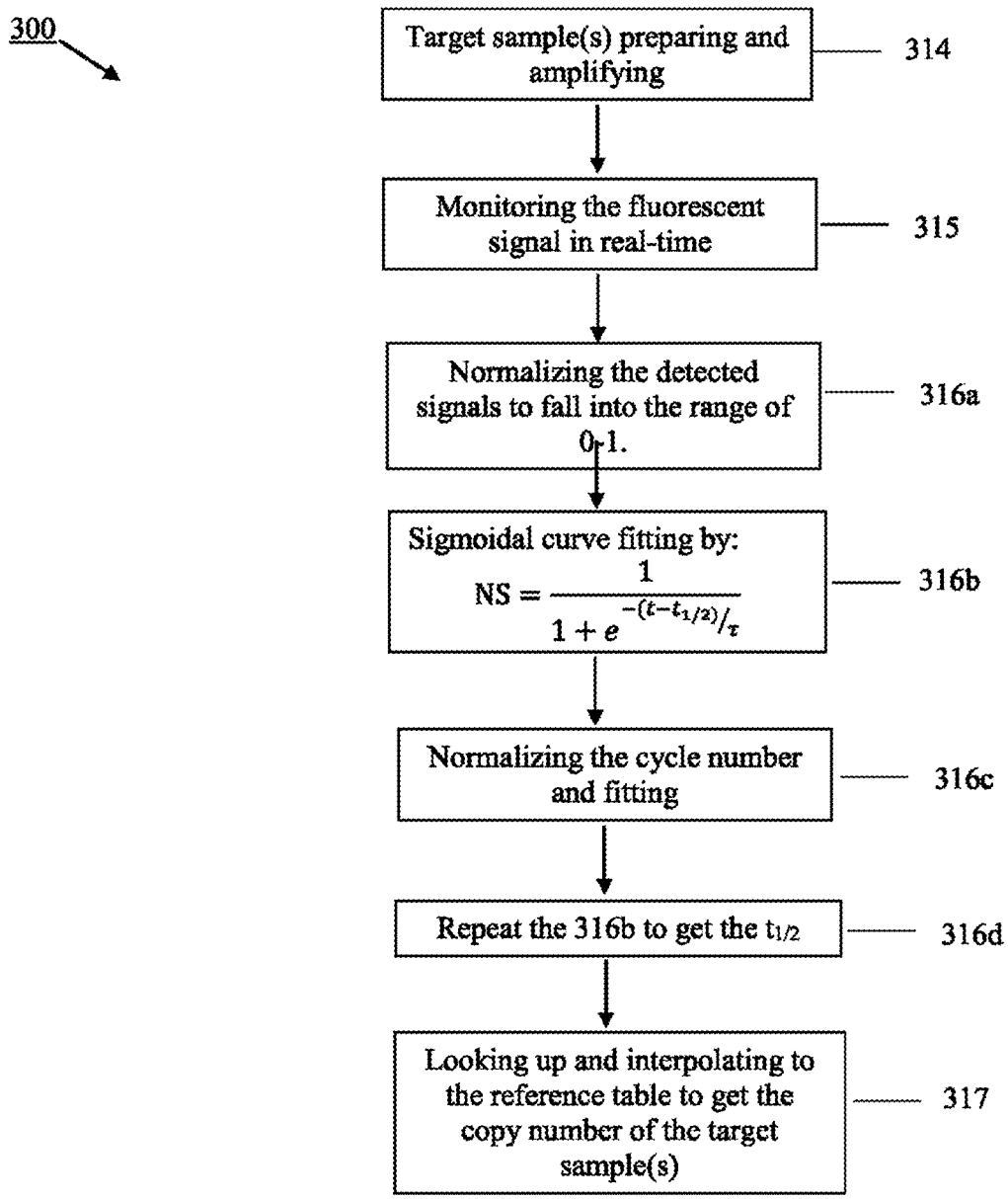
FIG. 3 illustrates the method to determine the copy number of the target sample.

The detected signals of reference samples and target sample (s) are analyzed by sigmoidal curve fitting function as shown in FIG. 2 and FIG. 3. It is because that the sigmoid function was shown to model PCR amplification more effectively than the exponential model upon which the threshold method is based. The two-parametric sigmoid function which is used to analyze the detected signals in this embodiment is as listed below:

$$NS = \frac{1}{1+e^{-(t-t_{1/2})/\tau}},$$

where NS is normalized fluorescent signal, t is cycle number, $t_{1/2}$ is the fractional cycle at which reaction fluorescence reaches half of the maximal reaction fluorescence, $\tau$ is the slope of the curve. The two variants are $t_{1/2}$ and $\tau$.

In this embodiment, the designated parameter is $t_{1/2}$. There are two operating parts of the embodiment. FIG. 2 illustrates the process of constructing a reference table of from the reference samples. FIG. 3 illustrates the process of getting the copy number of the target sample(s) by looking up and interpolating of the reference table. The user first prepares the reference table from the reference samples 200. The PCR amplification region of the reference samples, which share the same nucleic acid sequences within the target sample(s), are prepared 210, amplified and monitored by the fluorescence signals in real-time 211. Once the amplification completes, the detected signals are analyzed by-normalizing and sigmoidal curve fitting to get the $t_{1/2}$ 212a-212d. The reference table is then constructed by using the copy number vs. $t_{1/2}$ 213. The target sample (s) is/are then prepared and amplified under the same conditions as the reference samples 314, while measuring its amplification in real-time 315. After analyzing the detected signals of the target samples 316a-316d, the copy number(s) of the target sample(s) is/are known by looking up and interpolating the $t_{1/2}$ of the target sample (s) to the reference table 317.

The key procedures of detecting signals and analyzing the reference samples 212a-212d and the target sample(s) 312a-312d and their operating theories are listed as below:

a) After detecting the signals of the reference samples, subtracts the background value of each reference samples and then normalizes the variants of the fluorescent signal into the range of 0-1 212a. After this step, the fluorescent signal would become normalized. The purpose of this step is to reduce the inconsistent baseline signal which caused by reaction variations. (Such as the slight differences of light source or detector magnification, etc.)

Secondly, the normalized fluorescent signal and the cycle number are fitted into the two-parametric sigmoid function 212b. The $t_{1/2}$ and $\tau$ of each reference samples are obtained after this step. These two parameters, $t_{1/2}$ and $\tau$, represent the trend lines of all reference samples of this amplification. These two parameters provide the information of copy number and amplification efficiency of the reference samples.

c) Dividing the cycle number by $\tau$, the x-axis that records the cycle number is then normalized 212c. Since the amplification efficiencies vary under both situations, (1) for different qPCR operations, and (2) for each samples in amplified in one qPCR operation, it is hard to estimate the copy number. Therefore, this step is intended to relate the copy number solely to the normalized cycle number.

d) Re-fitting the curves of each reference samples into the sigmoid function 212d, the $t_{1/2}$ of each reference samples are obtained. $t_{1/2}$ are only related to the copy number. That is, $t_{1/2}$ will be different only when the copy number of each reference samples are different. The $t_{1/2}$ of each reference samples remain constants for different amplification efficiency.

e) Reference table 213 is organized by each $t_{1/2}$ which is corresponding to each of the different concentrations of the reference samples. After the reference table is constructed, if there is a need to quantify the target sample(s) which share the same nucleic acid sequence as the reference samples, the copy number of the target sample(s) can be obtained by comparing and interpolating to the reference table 317, which is got from the following steps for completing the amplification 314 of the target sample(s) to obtain the fluorescent signals 315, and processing the values to get the t½ of the target sample(s) with the same data processing steps 316a-316d.

The present invention is further elucidated by the following examples:

Example 1 Calibration of Different Primer Concentration

Step A. Amplification of UCP1 gDNAs 210 (Reference Samples)

The gDNA was isolated from whole blood using a QIAamp® DNA BLOOD Mini Kit (QIAGEN N.V.). The gDNA concentration was adjusted to 10 ng/μl (hereinafter, reference samples).

Primers having SEQ ID NO: 1 and SEQ ID NO: 2 were used to amplify a UCP1 sequence. The primer sequences are shown in Table 1. Two serial single dilutions were prepared from 0.4 μM with primer concentrations of 0.2 μM and 0.1 μM. As shown on Table. 2, for each amount of the primer, the experiment was performed in duplicatione.

TABLE 1

Primer Sequence
Primers used in the examples

| Sequence ID | Function | Sequence 5'-3' |
|---|---|---|
| SEQ ID No: 1 | Forward primer of UCP1 | CAGTTAAGAGCCTTTGCCAG |
| SEQ ID No: 2 | Reverse primer of UCP1 | TCCTTGGAATCCAGAACTAC |

The amplification reaction was carried out which was measured and monitored in real-time in the Evagreen® dye on a BioRad CFX Connect Real-time System (BioRad Laboratories, Inc.). Each reaction mixture volume was 25 μl, and was amplified under the following conditions:

TABLE 2

Conditions of the Amplification of the reference samples

|  | Condition 1 No. 1 & 2 | Condition 2 No. 3 & 4 | Condition 3 No. 5 & 6 |
|---|---|---|---|
| DNA template |  | gDNA 10 ng |  |
| Primer |  | UCP1-F1, UCP1-B1 |  |
| Primer | 0.4 μM | 0.2 μM | 0.1 μM |
| dNTP |  | 0.2 mM |  |
| EvaGreen ® |  | 0.25X |  |
| Polymerase |  | 1.25 unit |  |
| MgCl$_2$ |  | 3.5 mM |  |
| Total Volume |  | 25 μl |  |

The reaction mixtures were firstly incubated for 2 minutes at 94° C. The actual amplification reaction was carried out for 45 cycles according to the following scheme:

94° C. 10 sec.→60° C. 10 sec.→72° C. 15 sec.

Step B. Data Analyzing

Figure 4:
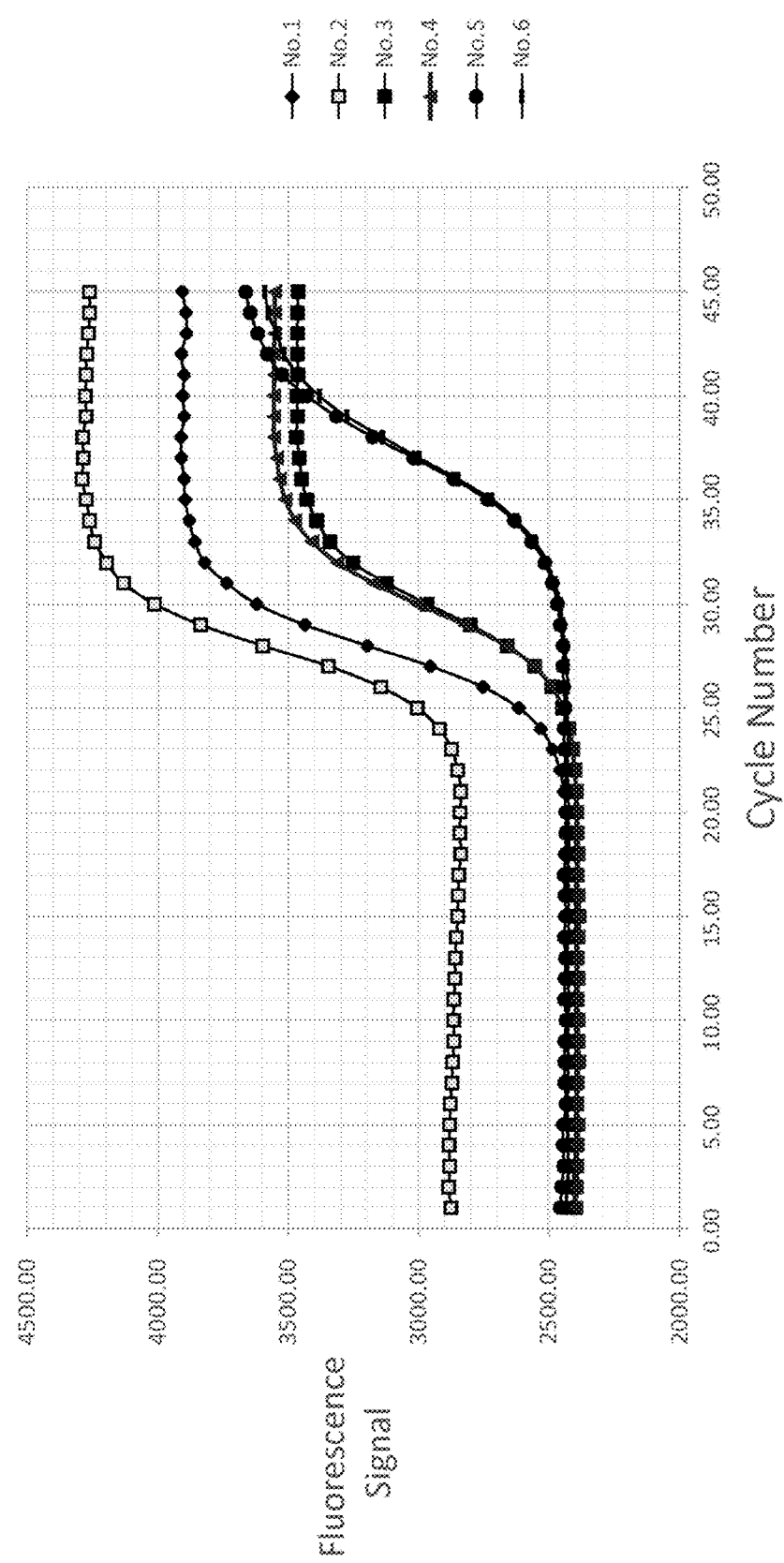
FIG. 4 shows the detected signals of the fluorescent signals of the EXAMPLE 1.
Figure 5:
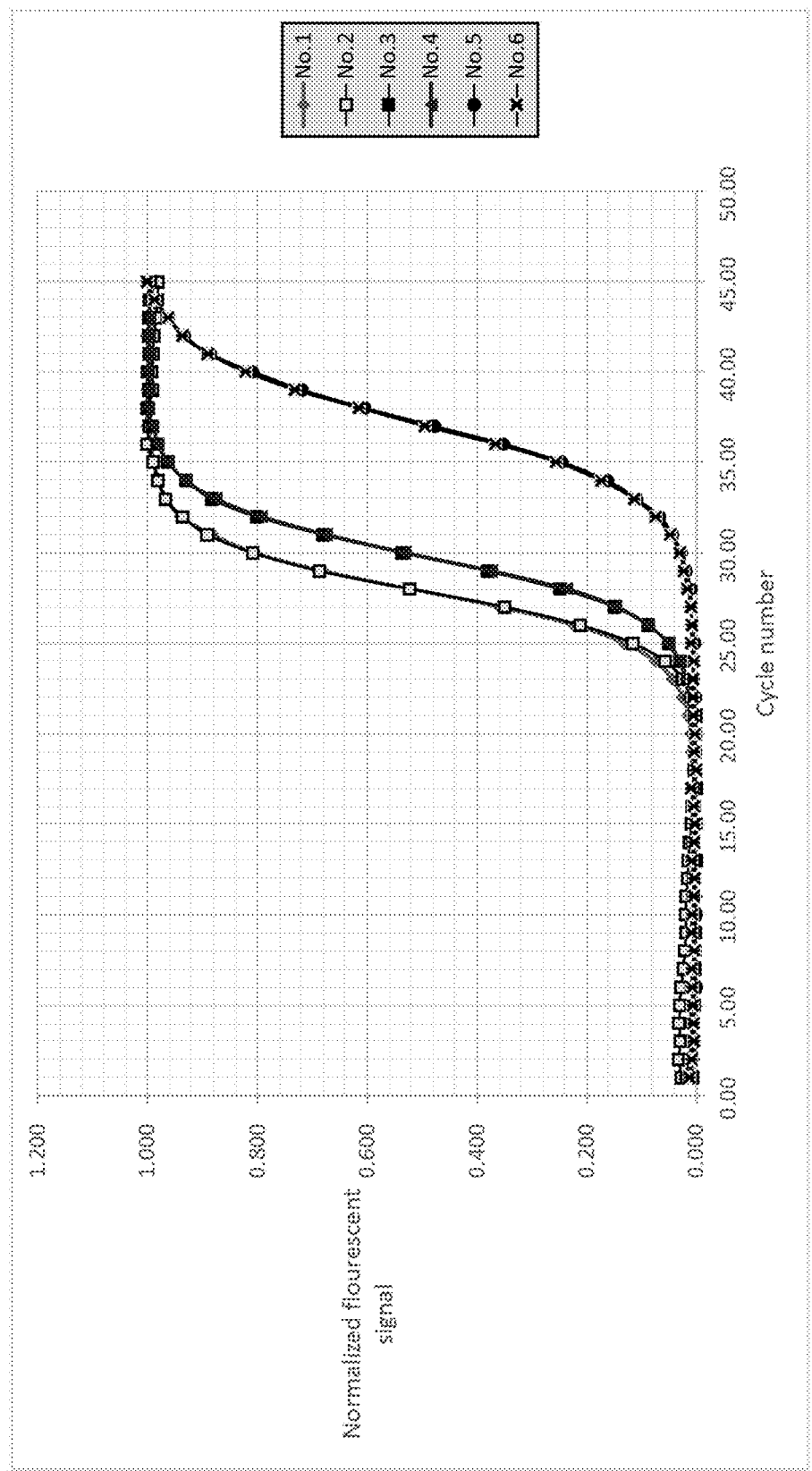
FIG. 5 shows the result of normalizing the fluorescent signal to fall into the range of 0-1 of EXAMPLE 1.

FIG. 4 shows the detected signals of the monitored fluorescence signals. As shown in FIG. 5, after detecting the signals of the reference samples, subtracts the background value of each reference samples and then normalizes the variants of the fluorescent signal into the range of 0-1 212a.

Figure 6:
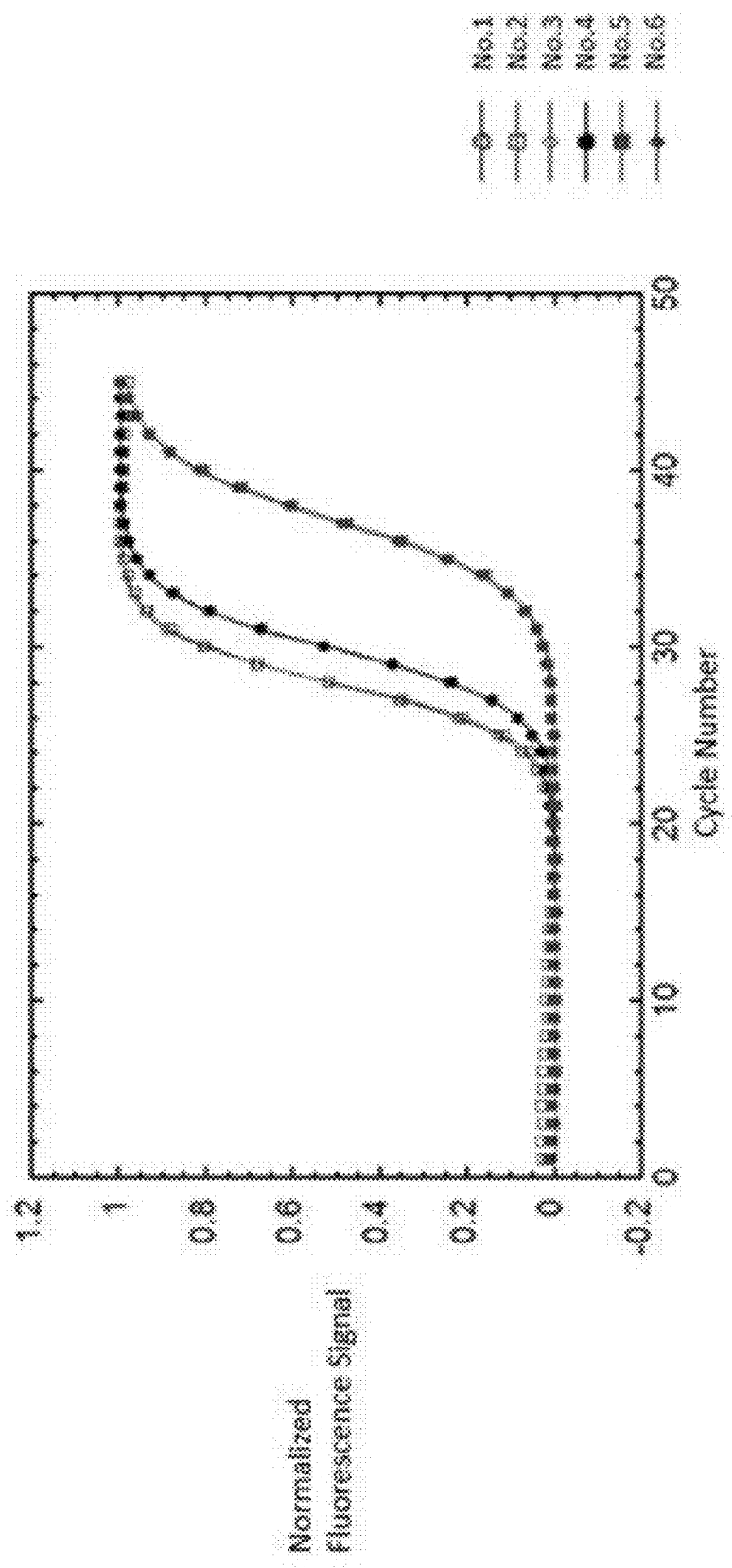
FIG. 6 shows the result of sigmoidal curve fitting of EXAMPLE

As shown in FIG. 6, the normalized fluorescent signal and cycle number are fitted by two-parametric sigmoid function 212b. The R-square in this step is greater than 0.999 (r>0.999). The t½ and τ of the reference samples is as listed below:

TABLE 3

$t_{1/2}$ and τ of each sample after sigmoidal curve fitting 212b

|  |  | $t_{1/2}$ | τ |
|---|---|---|---|
| No. 1 | 0.4 μM | 27.87 | 1.5239 |
| No. 2 | 0.4 μM | 27.9 | 1.4428 |
| No. 3 | 0.2 μM | 29.773 | 1.6063 |
| No. 4 | 0.2 μM | 29.826 | 1.614 |
| No. 5 | 0.1 μM | 37.16 | 1.9203 |
| No. 6 | 0.1 μM | 37.038 | 1.9301 |

Figure 7:
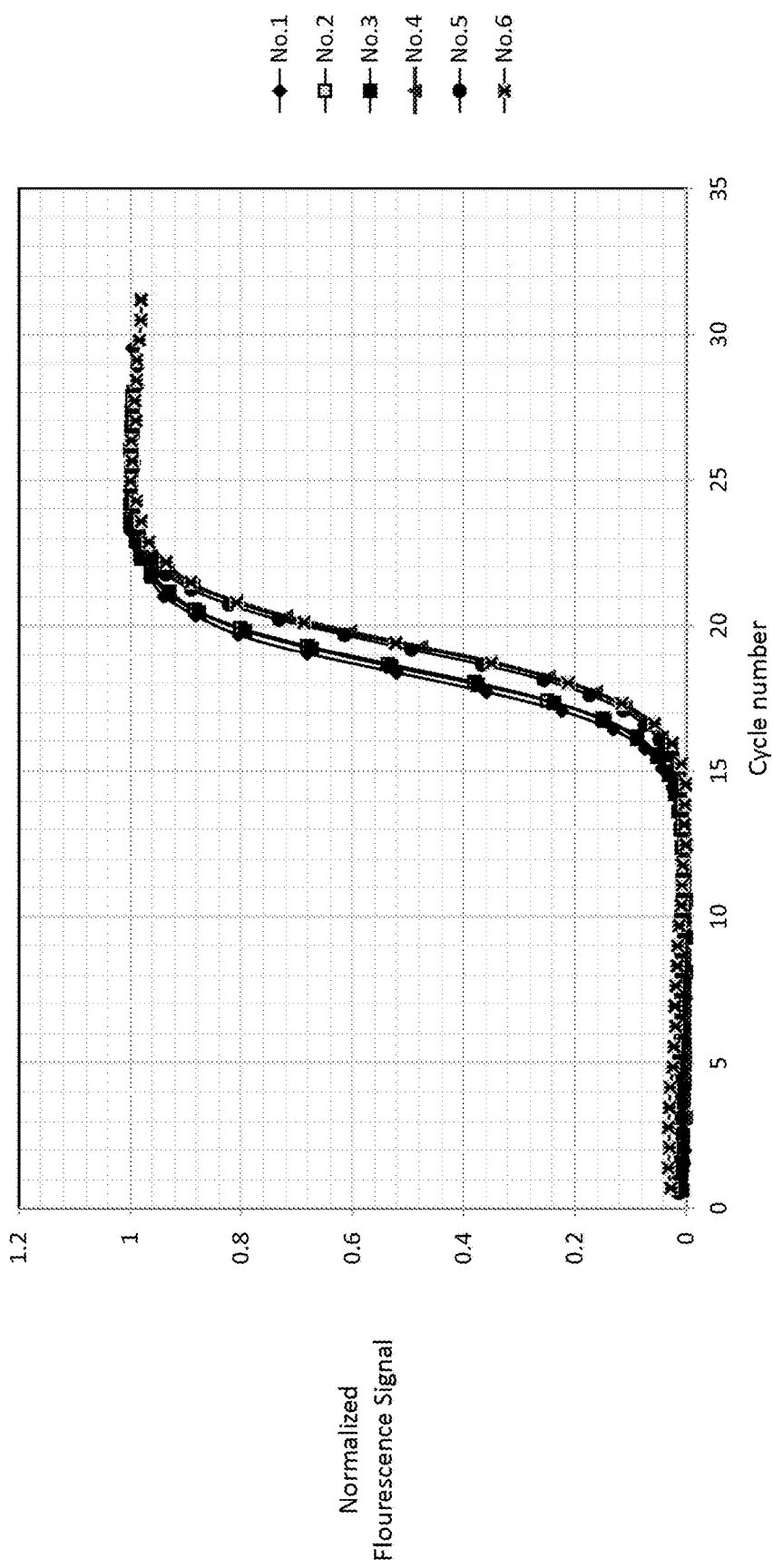
FIG. 7 shows the result of normalizing the cycle number and re-fitting of EXAMPLE 1.

As shown in FIG. 7, dividing the cycle number by τ, then each of the cycle number axis is normalized 212c. The R-square in this step is also greater than 0.999 (r>0.999). Re-fitting the curves of each reference samples by the sigmoid function 212d, and the $t_{1/2}$ of each reference samples are obtained and as listed in Table 4. The $t_{1/2}$ of each reference samples are not changed by different primer concentration.

TABLE 4

$t_{1/2}$ of each reference samples after normalization 212c.

|  |  | $t_{1/2}$ |
|---|---|---|
| No. 1 | 0.4 μM | 18.289 |
| No. 2 | 0.4 μM | 19.338 |
| No. 3 | 0.2 μM | 18.535 |
| No. 4 | 0.2 μM | 18.48 |
| No. 5 | 0.1 μM | 19.351 |
| No. 6 | 0.1 μM | 19.19 |

Example 2 Calibration of Different dNTP Concentration

Step A. Amplification of UCP1 gDNAs 210 (Reference Samples)

The conditions and the processes of gDNA extraction and amplification are identical with EXAMPLE 1 as listed in Table 5 except: a. two serial single dilutions were prepared from 0.4 mM with dNTP concentrations of 0.2 mM and 0.1 mM, b. the primer concentration is 0.4 μM.

TABLE 5

Conditions of the Amplification of the reference samples

|  | Condition 4 No. 7 & 8 | Condition 5 No. 9 & 10 | Condition 6 No. 11 & 12 |
|---|---|---|---|
| DNA template |  | gDNA 10 ng |  |
| Primer primer | | UCP1-F1, UCP1-B1 0.4 μM | |
| dNTP | 0.4 mM | 0.2 mM | 0.1 mM |

TABLE 5-continued

Conditions of the Amplification of the reference samples

|  | Condition 4 No. 7 & 8 | Condition 5 No. 9 & 10 | Condition 6 No. 11 & 12 |
|---|---|---|---|
| EvaGreen ® | | 0.25X | |
| Polymerase | | 1.25 unit | |
| MgCl$_2$ | | 3.5 mM | |
| Total Volume | | 25 μl | |

Step B. Data Analysis

Figure 8A:
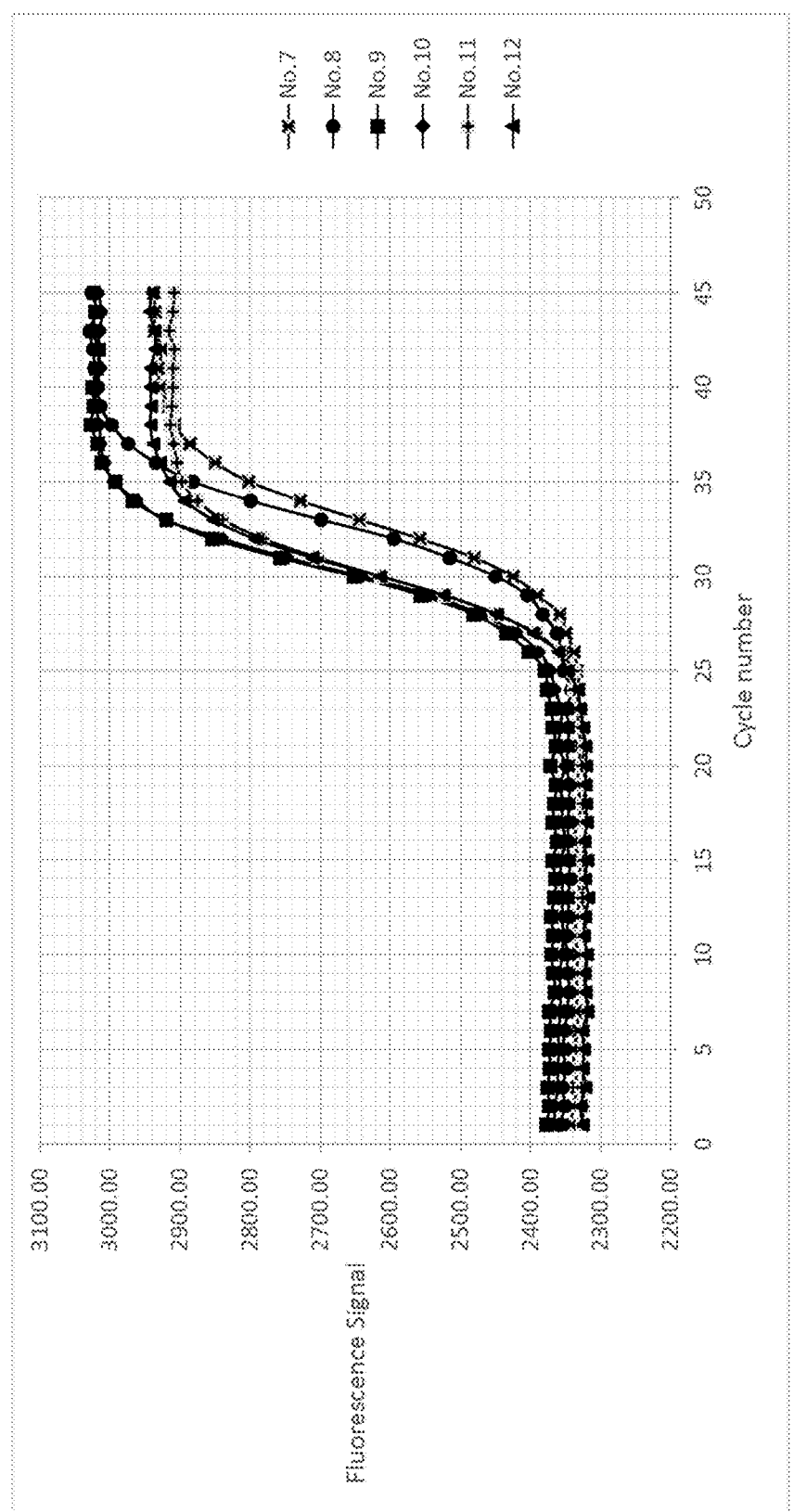
FIG. 8a-8d shows the result of normalizing and fitting processes of EXAMPLE 2.
Figure 8B:
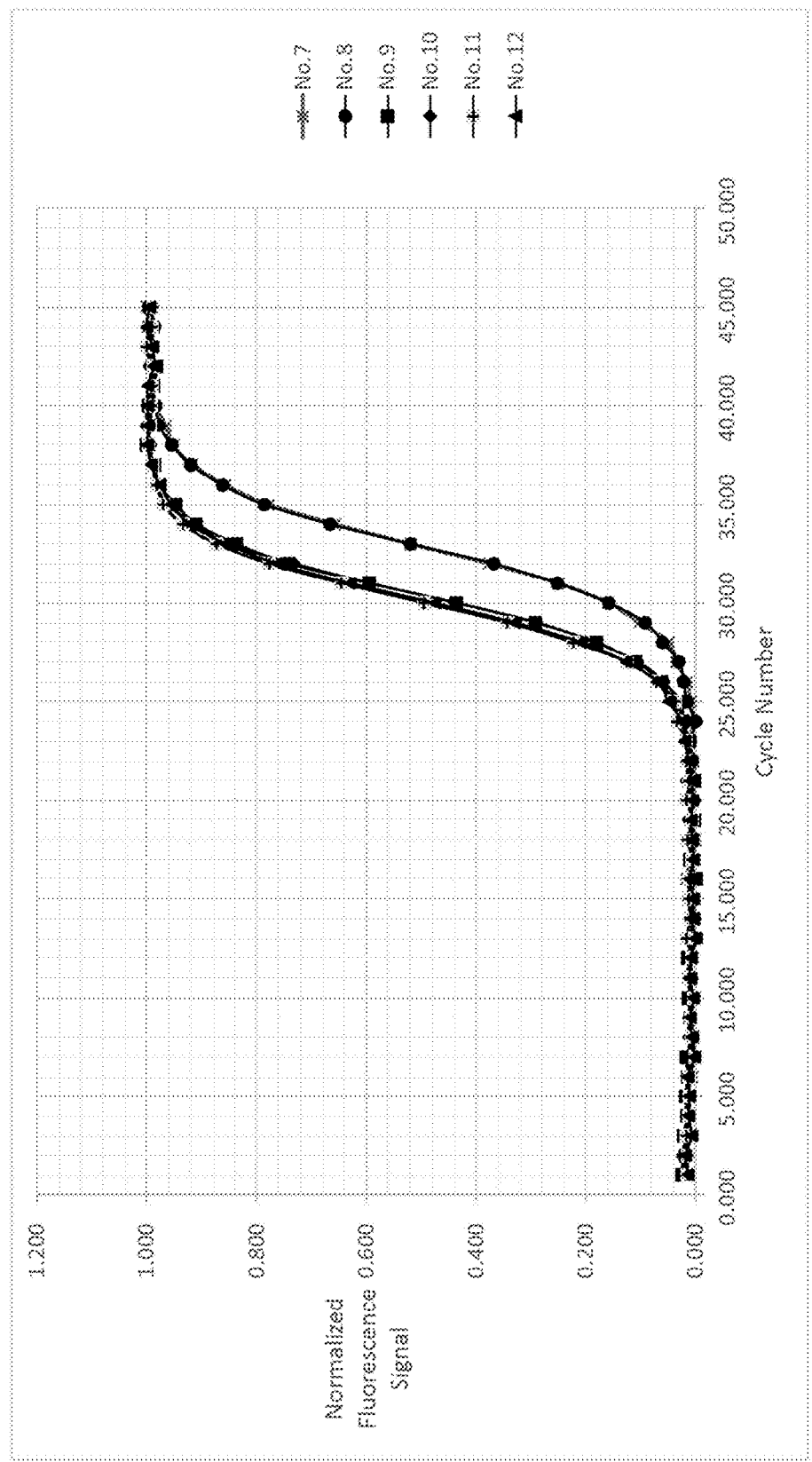
Figure 8C:
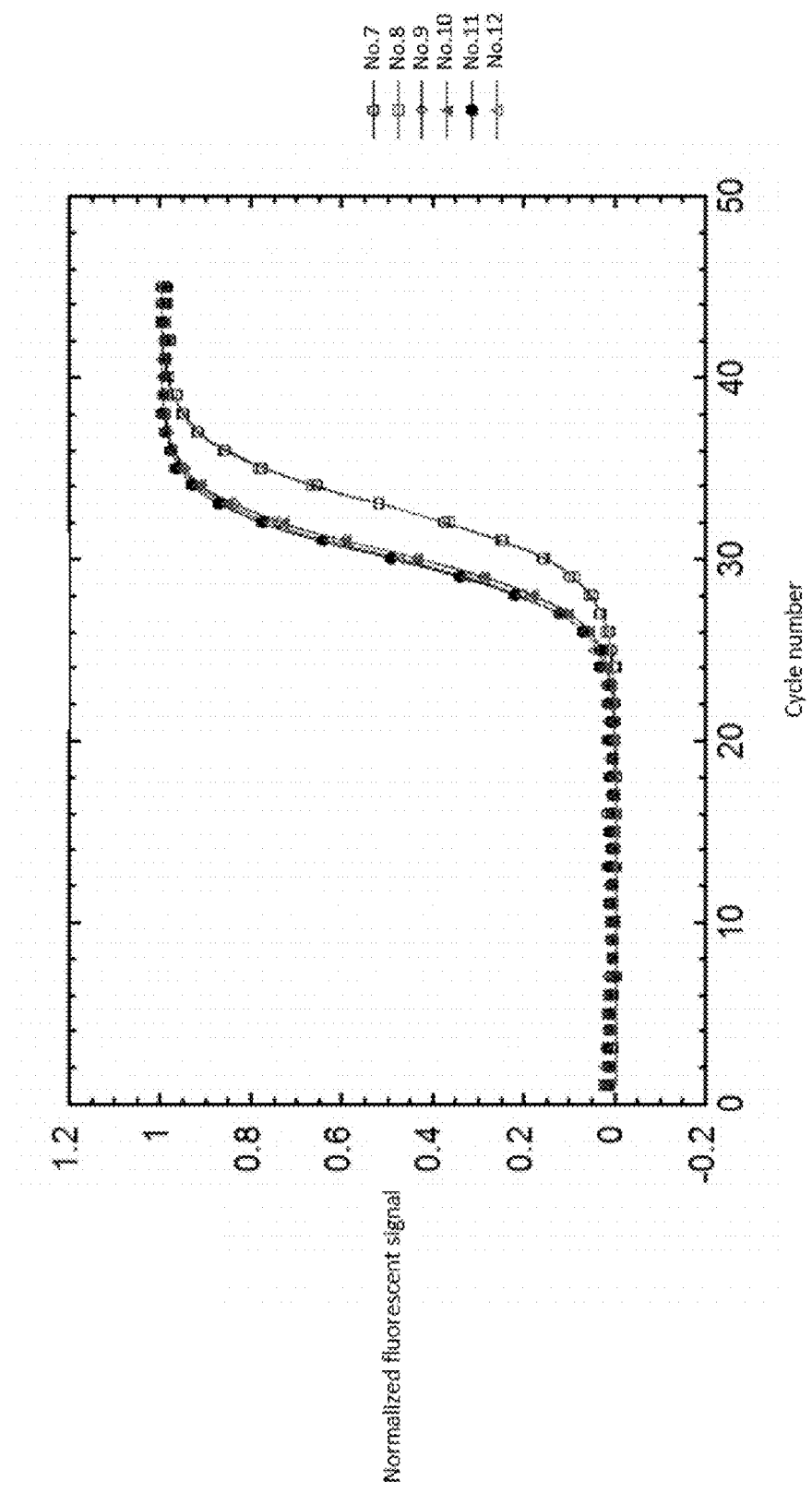
Figure 8D:
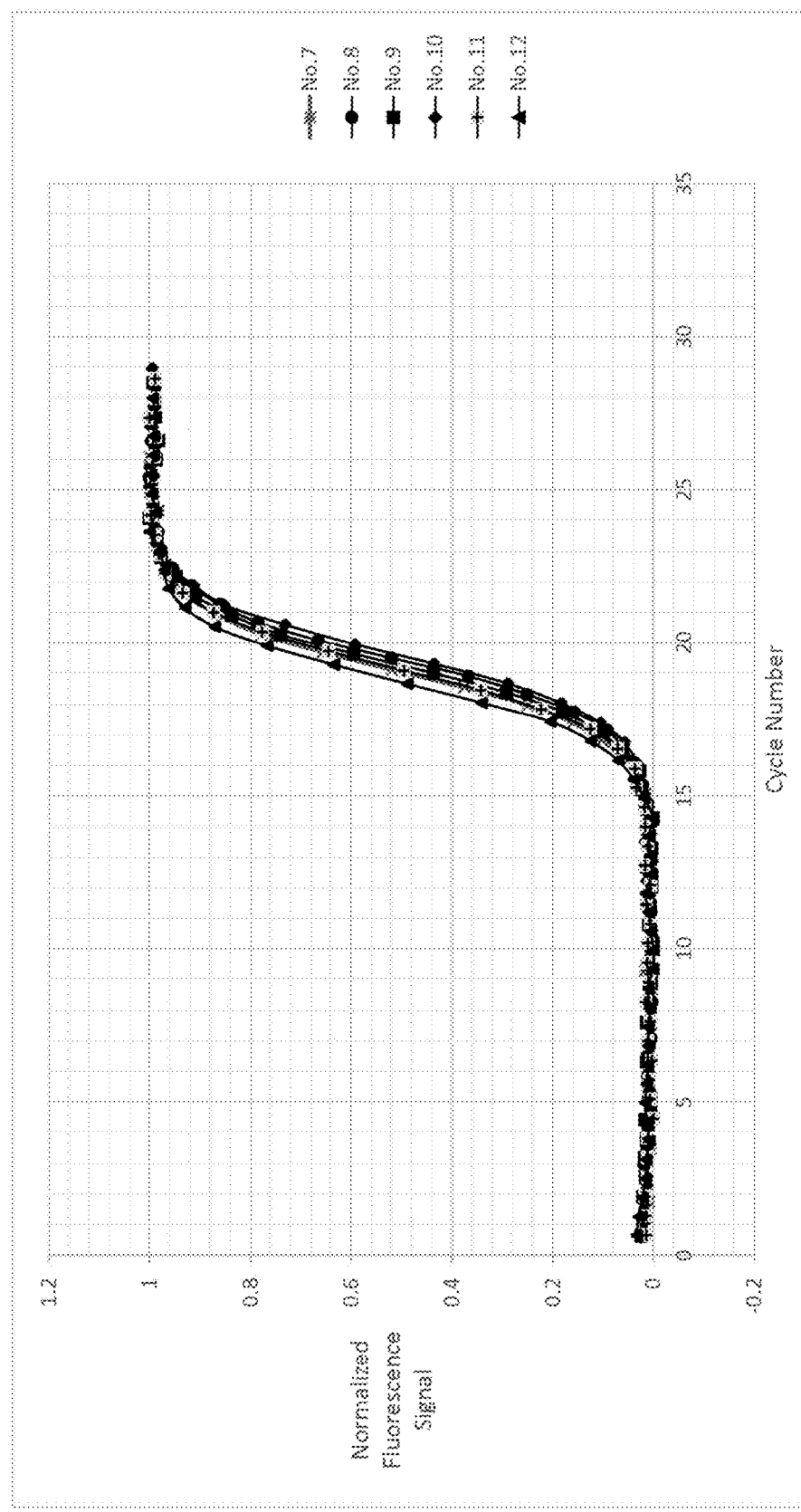

As shown in FIG. 8A-8D, analyzing the detected signals with the same processing step as shown in EXAMPLE 1, the obtained $t_{1/2}$ are only related to the copy number, and the $t_{1/2}$ of each reference samples are not changed by different dNTP concentrations. The detected signals are shown in FIG. 8A. FIG. 8B illustrates the background value subtraction of each reference samples and normalizing the variants of the fluorescent signal into the range of 0-1 212a. After normalizing the fluorescent signals, the normalized fluorescent signal and cycle number are fitted by the two-parametric sigmoid function 212b as shown in FIG. 8C. Each of the cycle number axis is normalized by dividing the cycle number by τ 212c. Re-fitting the curves of each reference samples by sigmoid function 212d. The results are shown in FIG. 8D.

Example 3 Reference Table Construction

Three different concentration templates are used in EXAMPLE 3 to construct a reference table of copy number vs. $t_{1/2}$.

Step A. Amplification of UCP1 gDNAs 210 (Reference Samples)

The gDNA was isolated from the whole blood by using a QIAamp® DNA BLOOD Mini Kit (QIAGEN N.V.). The gDNA concentration was adjusted to 10 ng/μl. Two serial single dilutions were prepared from this with gDNA concentration of 2.5 ng/μl, and 0.625 ng/μl.

Primers having SEQ ID NO:1 and SEQ ID NO:2 were used to amplify a UCP1 sequence. The primer sequences are already listed in Table 1. As shown in Table 6, for each amount of the gDNA, the experiment was performed in duplication. The amplification reaction was carried out and was measured and monitored in real-time in the Evagreen® dye on a BioRad CFX Connect Real-time System (BioRad Laboratories, Inc.). Each reaction mixture volume was 25 μl, and was amplified under the following conditions:

TABLE 6

Conditions of the Amplification of the reference samples

|  | Condition 7 No. 13 & 14 | Condition 8 No. 15 & 16 | Condition 9 No. 17 & 18 |
|---|---|---|---|
| DNA template | 10 ng | 2.5 ng | 0.625 ng |
| Primer primer | | UCP1-F1, UCP1-B1 0.4 μM | |
| dNTP | | 0.2 mM | |
| EvaGreen ® | | 0.25X | |
| Polymerase | | 1.25 unit | |
| MgCl$_2$ | | 3.5 mM | |
| Total Volume | | 25 μl | |

Step B. Data Analysis

Figure 9A:
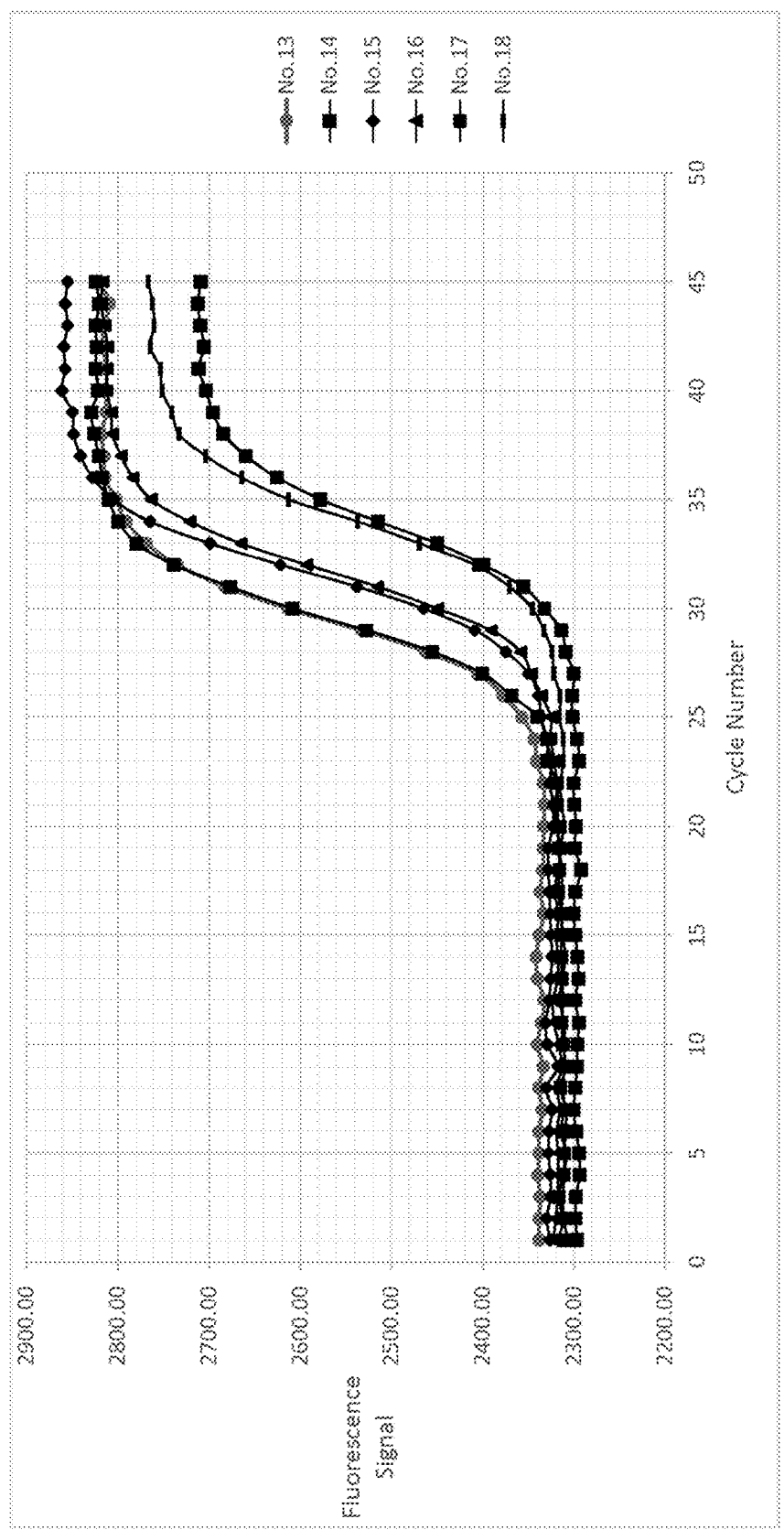
FIG. 9a-9d shows the result of normalizing and fitting processes of EXAMPLE 3.
Figure 9B:
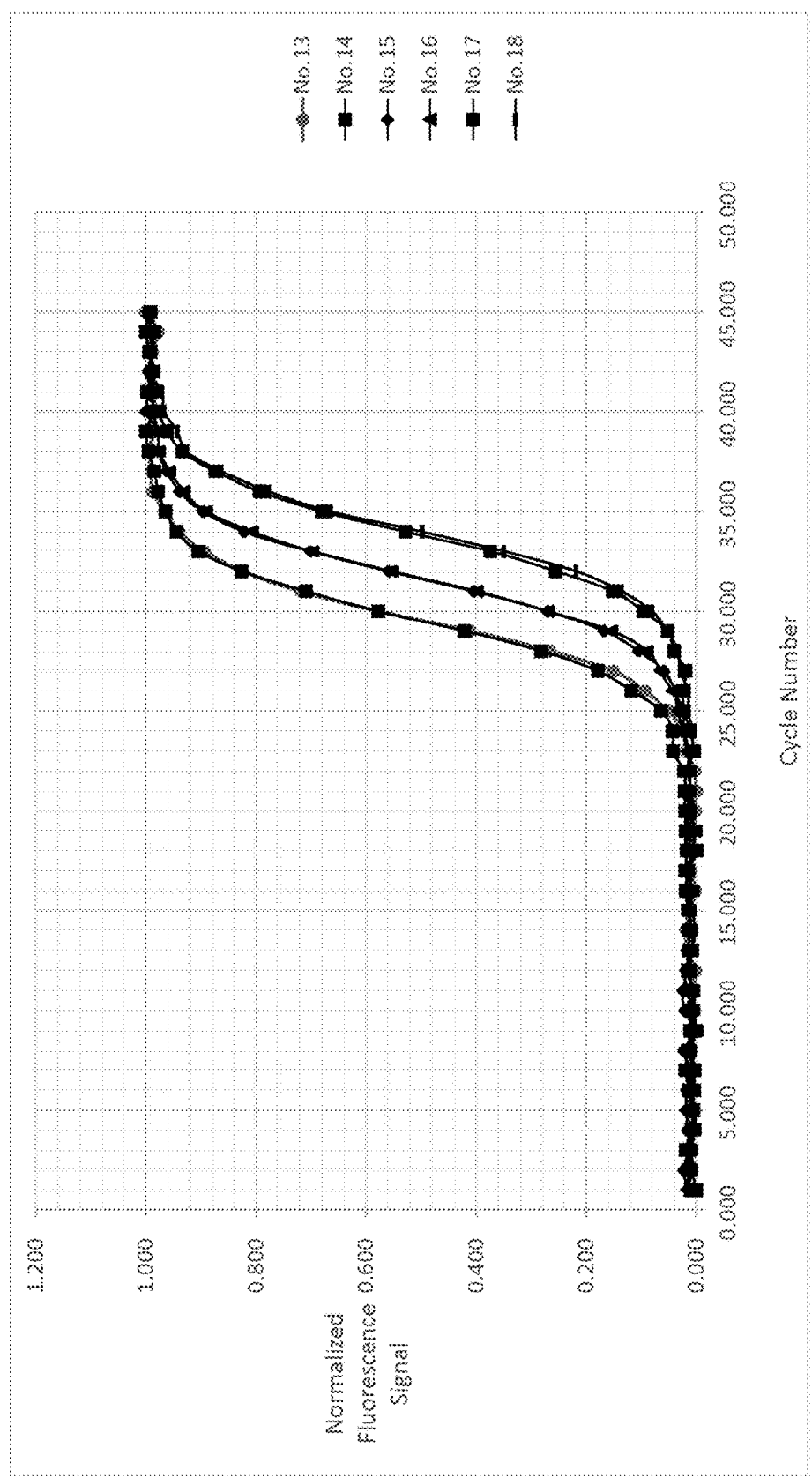
Figure 9C:
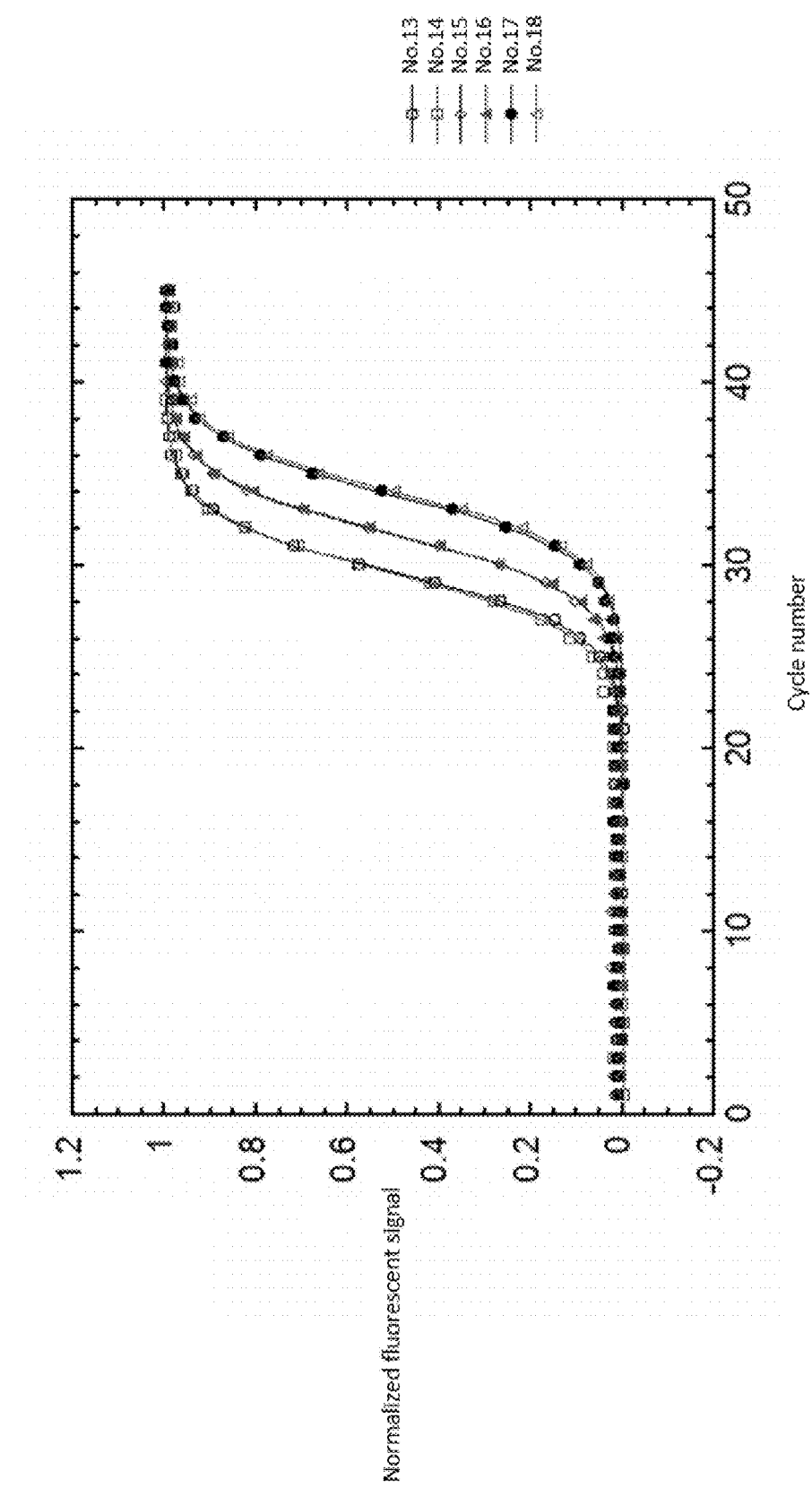
Figure 9D:
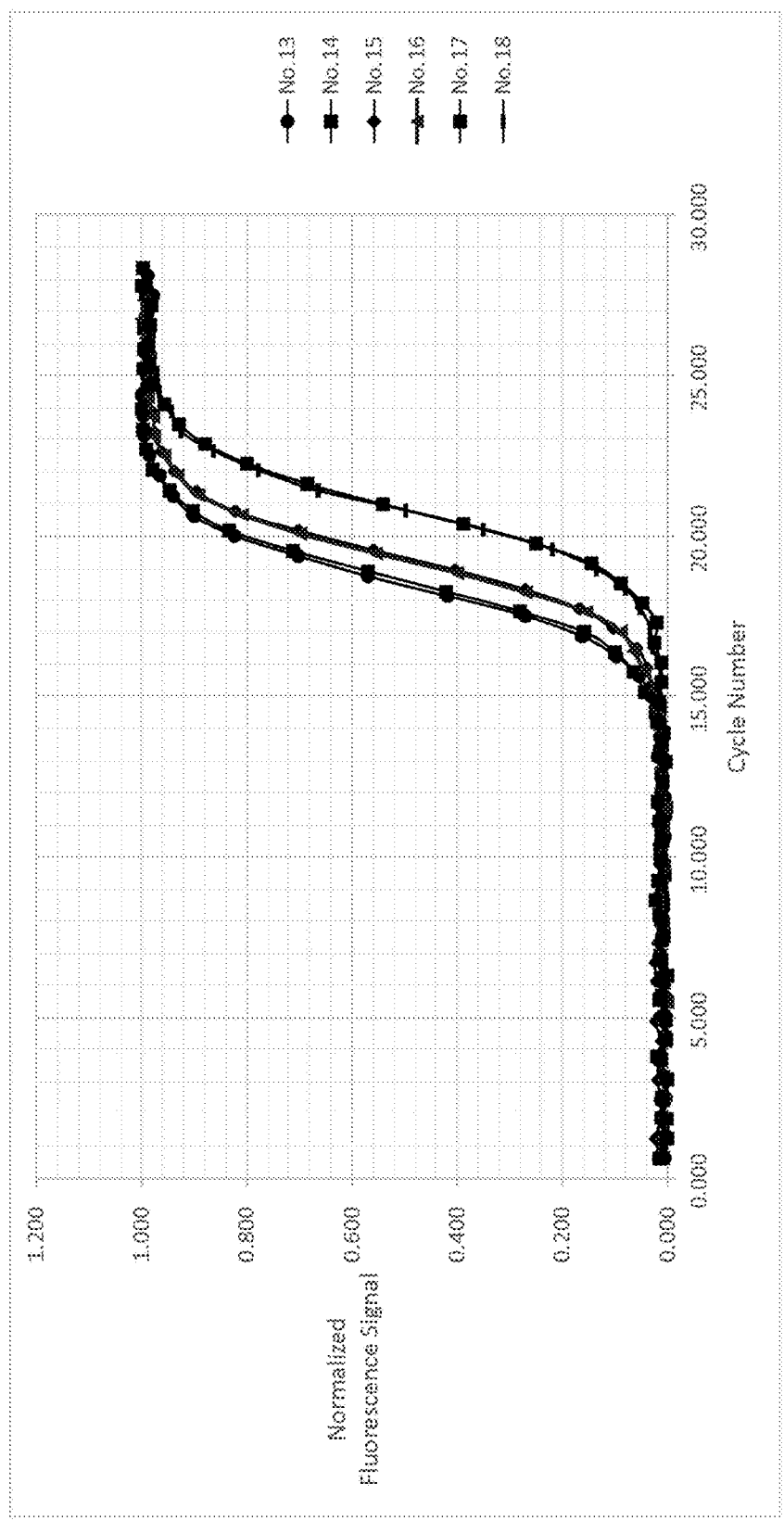

As shown in FIG. 9A-9D, analyzing the detected signals with the same processing step as EXAMPLE 1, the obtained $t_{1/2}$ are only related to the copy number. The detected signals are shown in FIG. 9A. FIG. 9B illustrates the background value subtraction of each reference samples and normalizing the variants of the fluorescent signal into the range of 0-1 212a. After normalizing the fluorescent signals, the normalized fluorescent signal and cycle number are fitted by two-parametric sigmoid function 212b as shown in FIG. 9C. The R-square in this step is greater than 0.999 (r>0.999). Each of the cycle number axis is normalized by dividing the cycle number by τ 212c. Re-fitting the curves of each reference samples by sigmoid function 212d. The results are shown in FIG. 9D.

The $t_{1/2}$ of each copy number are as shown in Table 7. They will only be different when the copy number differed.

TABLE 7

| The copy number of UCP-1 | $t_{1/2}$ |
|---|---|
| 0.625 ng | 18.280 |
| 2.5 ng | 19.217 |
| 10 ng | 20.580 |

Example 4 Target Sample Quantification

Taking a 5 ng gDNA as DNA template of the target sample, the amplification conditions and processes are identical with the reference samples in EXAMPLE 3. After amplifying the target sample 314, monitoring and detecting the fluorescent signal in real-time 315. The $t_{1/2}$ of the target sample is obtained after analyzing the detected signals with the same processing step as EXAMPLE 3 316a-316d.

The value of the $t_{1/2}$ of the target sample is 18.497. The copy number of the target sample is 4.03 ng after comparing and interpolating the obtained t½ to the reference table 317. The relative error is less than 20% to theoretic value.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for quantification of a target nucleic acid, comprising the steps of:
 (a) constructing a reference table of copy number vs. normalized cycle number from reference samples with the same nucleic acid sequence of the target nucleic acid, wherein the reference table is constructed by the steps of:
  i. preparing the reference samples;
  ii. amplifying the reference samples;
  iii. monitoring and detecting the amplifications of the reference samples in real-time;
  iv. normalizing the detected signals to fall into the range of 0-1 when the amplifications are saturated;
  v. fitting curves of serial dilution by using the sigmoidal function:

$$NS = \frac{1}{1 + e^{-(t-t_{1/2})/\tau}},$$

wherein NS is a normalized signal, t is a cycle number, $t_{1/2}$ is a fractional cycle at which a reaction light reaches half of the maximal reaction light, τ is a slope of the curve;
  vi. normalizing the cycle number of each reference sample by the slope of the curves themselves; and
  viii. repeating the step v. to get $t_{1/2}$ of each reference sample;
 (b) amplifying the target nucleic acid;
 (c) monitoring and detecting the amplification of the target nucleic acid in real-time;
 (d) normalizing the detected signals within the range of 0-1 when the amplification of the target nucleic acid is saturated;

(e) fitting the curve of the target nucleic acid by using the sigmoidal function:

$$NS = \frac{1}{1 + e^{-(t-t_{1/2})/\tau}},$$

wherein NS is a normalized signal, t is a cycle number, $t_{1/2}$ is a fractional cycle at which a reaction light reaches half of the maximal reaction light, $\tau$ is a slope of the curve;

(f) normalizing the cycle number of the target nucleic acid by the slope of the curve itself;

(g) repeating step (e) to get $t_{1/2}$ of the target nucleic acid; and (h) obtaining the copy number of the target nucleic acid contained in the sample by performing a look-up in the reference table, wherein the amplification reactions of the target nucleic acid and the reference samples are real-time PCR.

2. The method of claim 1, wherein the amplifications of the target nucleic acid and the reference samples are monitored and detected by an optical device or a chemical sensor.

3. The method of claim 2, wherein the chemical sensor is a hydrogen ion or a pyrophosphate.

4. The method of claim 2, wherein the amplifications of the target nucleic acid and the reference samples are monitored and detected by the optical device with the aid of a DNA-binding dye, an intercalating dye, a probe, or a molecular beacon.

5. The method of claim 2, wherein the optical device is a fluorescence signal detection device, and the DNA-binding dye emits a fluorescence signal detected by the fluorescence signal detection device upon interaction with double-stranded nucleic acid after excitation with light.

6. The method of claim 1, wherein the detected signal is a fluorescence signal.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Forward primer of UCP1

<400> SEQUENCE: 1
cagttaagag cctttgccag         20

<210> SEQ ID NO 2
<211> LENGTH: 20
<212> TYPE: DNA
<213> ORGANISM: Artificial Sequence
<220> FEATURE:
<223> OTHER INFORMATION: Reverse primer of UCP1

<400> SEQUENCE: 2
tccttggaat ccagaactac         20